(12) United States Patent
Borcherding et al.

(10) Patent No.: US 6,420,373 B1
(45) Date of Patent: Jul. 16, 2002

(54) 9-N-BICYCLIC NUCEOSIDE AGENTS USEFUL AS SELECTIVE INHIBITORS OF PROINFLAMMATORY CYTOKINES

(75) Inventors: David R. Borcherding, Loveland; Carl K. Edwards, III, West Chester; H. Randall Munson, Loveland, all of OH (US)

(73) Assignee: Merrell Pharmaceuticals Inc., Bridgewater, NJ (US)

(*) Notice: Subject to any disclaimer, the term of this patent is extended or adjusted under 35 U.S.C. 154(b) by 0 days.

(21) Appl. No.: 08/372,712

(22) Filed: Jan. 13, 1995

Related U.S. Application Data

(63) Continuation of application No. 08/097,340, filed on Jul. 23, 1993, now abandoned.

(51) Int. Cl.[7] .................... C07D 473/34; C07D 519/00; A61K 31/52; A61P 19/02
(52) U.S. Cl. ................ 514/261; 514/266; 544/264; 544/277; 546/118
(58) Field of Search ............... 544/264, 276, 544/277; 514/261, 266

(56) References Cited

U.S. PATENT DOCUMENTS

| 4,479,951 A | 10/1984 | Klessing et al. ............ 544/118 |
| 4,535,158 A | 8/1985 | Klessing ..................... 544/118 |
| 4,622,324 A | 11/1986 | Klessing et al. ............ 544/267 |
| 5,091,431 A | 2/1992 | Tulshian et al. ............ 544/276 |

OTHER PUBLICATIONS

Merek Manual, 16th Edition, pp. 72–74 (1993).*
Brynskov, New Eng J Med. 321, 845(1989).*
Wispe, J Clin Invest. 86, 1954 (1990).*
Cohen, Schweiz Med. Wschr 123, 492(1993).*
Fisher, Jr Critical Care Med 21, 318(1993).*
Craig, *BioWord Today*, Jul. 25, 1994, p. 1.*
Craig BioWorld Today Jul. 19, 1994, p. 1.*
Luke, Int. J. Clin Pharm, Ther 8 Tox. 31, 343(1993).*
Mankon Kaw Keyoon, Proc. Natl Acad Sci 90, 5974 (1993).*
Sampaio, J Exp Med. 173, 699–703 (1991).*
Danis Annals of Rheumatic Disease 51, 946 (1992.*
ODIO, New Eng J Med 324, 1525(1991).*
Nguyen, J Immunology, 144, 3822 (1990).*
Kay, Cellular Immun. 87, 217(1984).*
Sachar, New Eng J Med 321, 894 (1989).*
Shand, N. and Richardson, B., *Scand. J. Rheumatol.* [Suppl.], 1988: 76:265–278.

\* cited by examiner

*Primary Examiner*—Mark Berch
(74) *Attorney, Agent, or Firm*—T. Helen Payne; Paul R. Darkas

(57) ABSTRACT

The present invention relates to novel 9-N-bicyclic nucleoside agents which are useful as selective inhibitors of proinflammatory cytokines.

33 Claims, No Drawings

9-N-BICYCLIC NUCEOSIDE AGENTS USEFUL AS SELECTIVE INHIBITORS OF PROINFLAMMATORY CYTOKINES

This is a continuation, division, of application Ser. No. 08/097,340, filed Jul. 23, 1993, abandoned, which is herein incorporated by reference.

BACKGROUND OF THE INVENTION

Autoimmune and inflammatory diseases affect more than fifty million Americans. As a result of basic research in molecular and cellular immunology over the last ten to fifteen years, approaches to diagnosing, treating and preventing these immunological based diseases has been changed forever. By dissecting the individual components of the immune system, those cells, receptors and mediators which are critical to the initiation and progression of immune responses have been, and continue to be, elucidated. Crystallographic analysis of proteins encoded in the major histocompatability complex, identification of an antigen-specific T cell receptor, and development of a basic understanding of the complex cytokine network have all contributed to a revolution in immunology. Equipped with this new and fundamental information about basic immune mechanisms, selective and rational approaches to the treatment of inflammatory and autoimmune disease can now be developed.

Until the last decade, treatment of immunological based disorders were treated exclusively with nonspecific immunosuppressive agents. These included a variety of drugs, such as corticosteroids, antimalarials, methotrexate, azathioprine, and treatments such as total lymphoid irradiation. Although some of these approaches may affect one component of the immune response more than another, they remain nonspecific in their actions and treatment frequently is complicated by serious side effects. It would be very useful to discover and develop new drugs which are immune cell selective or mediator specific and which interfere with processes critical to the initiation, progression, and maintenance of the acute and chronic inflammatory processes associated with certain immunological based diseases.

The two most important cells of the immune response in the autoimmune and inflammatory processes are the T lymphocyte and the monocyte/macrophage.

The T cell is critical to all antigen driven cellular immune responses. There are at least two major subpopulations of T cells: T helper (CD4$^+$) and T cytotoxic (CD8$^+$). T cells recognize antigen via a unique membrane receptor: the T cell antigen receptor (TCR). The TCR can recognize antigen only in association with cell surface proteins known as major histocompatibility complex (MHC) molecules. In response to antigen presented by MHC class II molecules, T helper cells secrete a variety of soluble factors, collectively known as lymphokines. Lymphokines play an essential role in the activation, differentiation, and expansion of all the cells of the immune response. In contrast to the T helper cell, the T cytotoxic cell responds to antigen in the context of MHC class I molecules. Cytotoxic T lymphocytes, once activated, can eliminate cells displaying a specific antigen derived from a virus, tumor cell, or foreign tissue graft.

Mononuclear phagocytic macrophages are widely distributed throughout the body and display great structural and functional heterogeneity. Macrophages are derived from circulating monocytes which migrate into extravascular tissues. The migration of peripheral blood monocytes involves adherence to the endothelium, migration between endothelial cells, and subsequently movement through subendothelial structures. Adherence of monocytes to endothelium involves high molecular weight glycoproteins, such as lymphocyte function-associates antigen 1 (LFA-1; CDlla/CD18), which interacts with intercellular adhesion molecule-1 (ICAM-1; CD54) present on vascular endothelial cells. Monocytes and macrophages produce a variety of pro-inflammatory mediators (cytokines), such as interleukin-1 (IL-1), interleukin-6 (IL-6) and tumor necrosis factor (TNF). These cytokines have numerous effects on many cells within and outside the immune system, such as promoting activation, differentiation, expansion, or apoptosis. In addition, cytokines such as IL-1 increase the expression of adhesion molecules like ICAM-1 and greatly facilitate monocyte migration to the inflammatory site. Furthermore, the monocyte/macrophage is one of the major types of antigen presenting cells required for T helper cell activation.

During the last decade, an understanding of immunopathological reactions has greatly evolved as a result of the characterization of cytokines and interleukins which regulate interactions between cells of the immune system and other nonimmune tissues and cells such as endothelial cells, fibroblasts and adipocytes. A major cytokine increasingly recognized as a central mediator in a wide spectrum of physiologic and immune functions is macrophage-derived Tumor Necrosis Factor-α, also known as TNF-α, or Cachectin. TNF-α has been found to mediate effects as diverse as tumoricidal activity, wasting and weight loss associated with chronic disease, promotion of cartilage erosion and the destruction of joints in rheumatoid arthritis, and the recruitment of cells to participate more effectively in the host's response to an invasive agent. In addition, an increasingly large body of evidence indicates that TNF-A serves as the proximal mediator in the evolution of septic shock.

The biological function of TNF-α extends well beyond its initial discovery as a mediator of tumor necrosis. It is increasingly realized that the interacting milieu of host cytokines existing locally and systemically is an extremely important network that dictates the pathogenesis of many immune and inflammatory diseases. TNF-α appears to play a critically important role in this regard because of its ability to activate a wide range of cell types in order to promote production of several key cytokines (e.g. IL-1β, IL-1α and IL-6), bioactive eicosanoids, and platelet activating factor (PAF).

Enhanced synthesis and release of cytokines has been observed during many acute and chronic inflammatory processes, and it is increasingly realized that in many cases, overproduction of TNF-α is a major contributor to inflammation, cellular injury, and cell death associated with various immunological based diseases.

There is now evidence to indicate that TNF-α is a primary mediator of septic shock. TNF-α, along with other cytokines, triggers inflammatory and metabolic responses attributed to sepsis and septic shock including adult respiratory distress syndrome (ARDS), fever, and disseminated intravascular coagulation. ARDS is characterized by increased pulmonary capillary permeability resulting in non-cardiogenic pulmonary edema, decreased lung compliance and decreased lung volume. Although ARDS is frequently associated with sepsis, it also occurs as a result of smoke inhalation, pancreatitis and long-bone fractures.

Patients infected with the human immunodeficiency virus (HIV) enter a long period of clinical latency prior to developing clinically apparent disease. HIV infects T cells as well as monocytes and macrophages, and activation of latent or marginally active HIV infected cells may be promoted in part by cytokines, including TNF-α. TNF-α has also been implicated in the pathogenesis of fever, cachexia (wasting syndrome), and *Myobacterium tuberculosis* infections in patients with acquired immunodeficiency syndrome (AIDS).

Cytokines, including TNF-α, are known to play an important role in the pathogenic processes of inflammatory bowel disease. Ulcerative colitis and Crohn's disease are two common forms of inflammatory bowel disease.

Complex patterns of interacting cytokines, including TNF-α, and products of arachidonic acid metabolism produced locally in the central nervous system have been implicated in contributing to adverse sequelae of bacterial meningitis.

Rheumatoid arthritis is a heterogenous, systemic disease of unknown etiology, and persons with rheumatoid arthritis typically develop inflammation of joint synovium (synovitis). Clinical symptoms become apparent with progression of synovitis due to production and release of cytokines from activated macrophages along with activation of T lymphocytes, angiogenesis, and attraction of neutrophils to the joint cavities. Cytokines induce synovial cell proliferation, resulting in invasion and destruction of articular cartilage. Synovial fibroblasts are thought to become activated by proinflammatory mediators such as TNF-α to secrete a large variety of cytokines and growth factors. TNF-α activity in rheumatoid arthritis includes recruitment and activation of PMNL leukocytes, cellular proliferation, increased prostaglandin and matrix-degrading protease activity, fever, and bone and cartilage resorption. TNF-α and TNF-α-induced IL-1 induce synthesis of collagenase and stromelysin by synoviocytes, contributing to loss of normal joint integrity and function.

Other diseases/syndromes in which TNF-α is implicated are vascular injury/atherosclerosis, diabetes mellitus type I, Kawasaki disease, leprosy, multiple sclerosis, anemia of chronic disease, ultraviolet radiation, *Helicobacter pylori* gastritis/ulcer disease, paracoccidioidomycosis, septic melioidosis, heart failure, familial Mediterranean fever, toxic shock syndrome, chronic fatigue syndrome, allograft rejection, Graft-versus-host disease, Schistosomiasis.

Thus, it would be very useful to provide a means for inhibition of TNF-α activity in a variety of disease states. The present invention now provides a means for inhibition of TNF-α activity. This provides a treatment for patients suffering from acute and chronic inflammatory processes associated with various immunological based diseases including septic shock, ARDS, inflammatory bowel disease including ulcerative colitis and Chrohn's disease, bacterial meningitis, rheumatoid arthritis, fever/cachexia (wasting syndrome)/*Myobacterium tuberculosis* infections in patients with AIDS, vascular injury/atherosclerosis, diabetes mellitus type I, Kawasaki disease, leprosy, multiple sclerosis, anemia of chronic disease, ultraviolet radiation, *Helicobacter pylori* gastritis/ulcer disease, paracoccidioidomycosis, septic melioidosis, heart failure, familial Mediterranean fever, toxic shock syndrome, chronic fatigue syndrome, allograft rejection, Graft-versus-host disease, Schistosomiasis. In addition, the present invention provides a treatment which inhibits the activation of latent or marginally active HIV infected cells in patients with AIDS.

SUMMARY OF THE INVENTION

The present invention provides compounds having the following general formula (I):

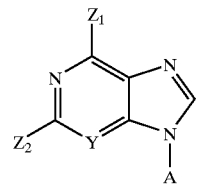

formula (I)

wherein
  Y is nitrogen or CH;
  $Z_1$ and $Z_2$ are each independently hydrogen, halogen or $NH_2$; and
  A is selected from the group consisting of:

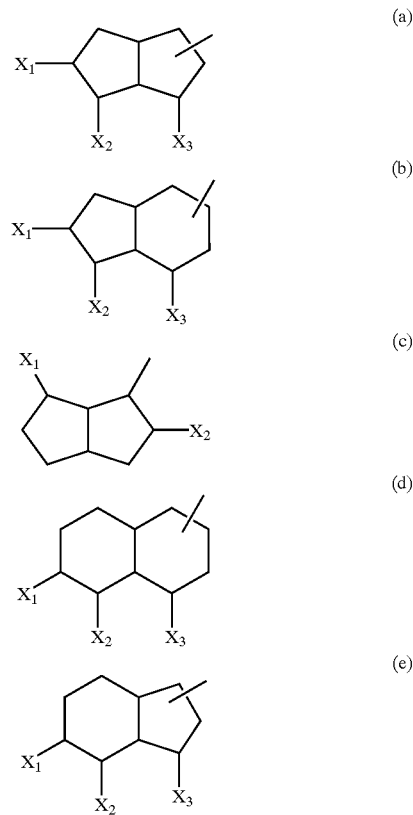

wherein $X_1$, $X_2$ and $X_3$ are each independently hydrogen, OH, $N_3$, $NH_2$, $N(R)_2$, NHR, CN, $CH_2NH_2$, $CONH_2$, $CO_2H$, $CH_2OH$, SH or SR;
  wherein R is $C_1$–$C_4$ alkyl; and
the pharmaceutically acceptable salts thereof;
with the proviso that at least one of $X_1$, $X_2$ or $X_3$ is other than hydrogen and with the further proviso that when $Z_1$ is $NH_3$; $Z_2$ is H or $NH_2$; A is

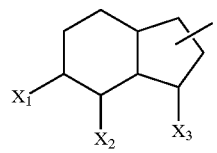

$X_3$ is H or OH; $X_2$ is H; then $X_1$ is not $CO_2H$.

The present invention further provides compounds having the following general formula:

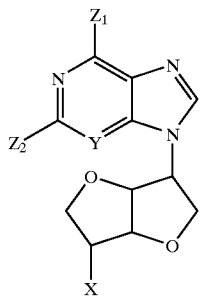

formula (II)

wherein
Y is nitrogen or CH;
Z₁ and Z₂ are each independently hydrogen, halogen or NH₂; and
X is $N_3$, $NH_2$, $N(R)_2$, NHR, CN, $CH_2NH_2$, $CONH_2$, $CO_2H$, $CH_2OH$, SH or SR;
  wherein R is $C_1$–$C_4$ alkyl; and
the pharmaceutically acceptable salts thereof.

The present invention further provides a method of inhibiting the TNF-α activity in a patient in need thereof comprising administering to said patient an effective antiinflammatory amount of a compound of formulas (I) or (II) or of formula (III);

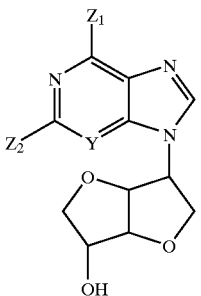

formula (III)

wherein
Y is nitrogen or CH;
Z₁ and Z₂ are each independently hydrogen, halogen or NH₂; and
the pharmaceutically acceptable salts thereof.

The present invention further provides a method of treating a patient suffering from septic shock comprising administering to said patient an effective immunosuppressant amount of a compound of formulas (I), (II) or (III).

DETAILED DESCRIPTION OF THE INVENTION

As used herein the term "$C_1$–$C_4$ alkyl" refers to a saturated straight or branched chain hydrocarbon radical of one to four carbon atoms. Included within the scope of this term are methyl, ethyl, n-propyl, isopropyl, n-butyl, isobutyl, and the like. The term "halogen" or "halo" refers to a chlorine, bromine or iodine atom. The term "Pg" refers to a protecting group such as isopropyldimethylsilyl, tert-butyldiphenylsilyl, methyl-di-tert-butylsilyl, tert-butyldimethylsilyl, benzyl, p-methoxybenzyl, o-nitrobenzyl, p-nitrobenzyl, p-chlorobenzyl, triphenylmethyl, methoxymethyl, 2-methoxyethoxymethyl, acetate and benzoate. The term "Lg" refers to a leaving group such as methanesulfonate, trifluoromethanesulfonate, p-toluenesulfonate, 2-nitrobenzenesulfonate, 3-nitrobenzenesulfonate, 4-nitrobenzenesulfonate or 4-bromobezenesulfonate and the like. It is understood in the art that a protecting group can function as a leaving group and a leaving group can function as a protecting group depending upon the reaction conditions utilized.

The terms "Ms" or "mesylate" refers to a methanesulfonate functionality of the formula:

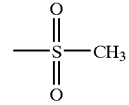

The terms "Ts" or "tosylate" refers to a p-toluenesufonate functionality of the formula:

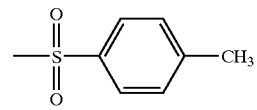

The term "pharmaceutically acceptable salt" refers to those salts that are not substantially toxic at the dosage administered to achieve the desired effect and do not independently possess significant pharmacological activity. The salts included within the scope of this term are hydrobromide, hydrochloride, sulfuric, phosphoric, nitric, formic, acetic, propionic, succinic, glycolic, lactic, malic, tartaric, citric, ascorbic, α-ketoglutaric, glutamic, aspartic, maleic, hydroxymaleic, pyruvic, phenylacetic, benzoic, p-aminobenzoic, anthranilic, p-hydroxybenzoic, salicyclic, hydroxyethanesulfonic, ethylenesulfonic, halobenzenesulfonic, toluenesulfonic, naphthalenesulfonic, methanesulfonic, sulfanilic, and the like. Hydrochloride is preferred as the pharmaceutically acceptable salt of compounds of formulas I, II and III.

It is understood that these compounds of formulas (I), (II) and (III) may exist in a variety of stereoisomeric configurations wherein the substituents $X_1$, $X_2$ and $X_3$ on A of formula (I), substituent X of formula (II) and the hydroxyl on formula (III) may be in the Endo or Exo configuration relative to the bicyclic ring of formula (IV)

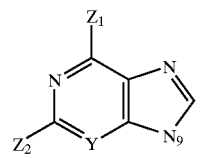

formula (IV)

wherein the substituents are as previously defined and A is connected to the ring at the 9-position of formula (IV).

It is further understood that the bicyclic ring compounds defined by A may exist in the CIS or TRANS configuration about the ring juncture. For example the 5—5 ring system may have the following configuration

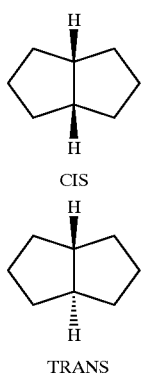

CIS

TRANS

It is further understood that where the relative configuration is fixed, the maximum number of enantiomers possible for each compound is equal to 2n wherein n represents the total number of chiral centers located on the compound and can be the integer 1, 2, 3 or 4 depending upon the substitution present on the compound. These stereoisomers, including the enantiomers are specifically understood to be included within the scope of the present invention.

The compounds of formula (I) wherein $X_1$, $X_2$ and $X_3$ are each independently H or OH can be prepared as described in Scheme I with the proviso that at least one of $X_1$, $X_2$ or $X_3$ is other than hydrogen. All the substituents, unless otherwise indicated, are previously defined. The reagents and starting materials are readily available to one of ordinary skill in the art.

Scheme I

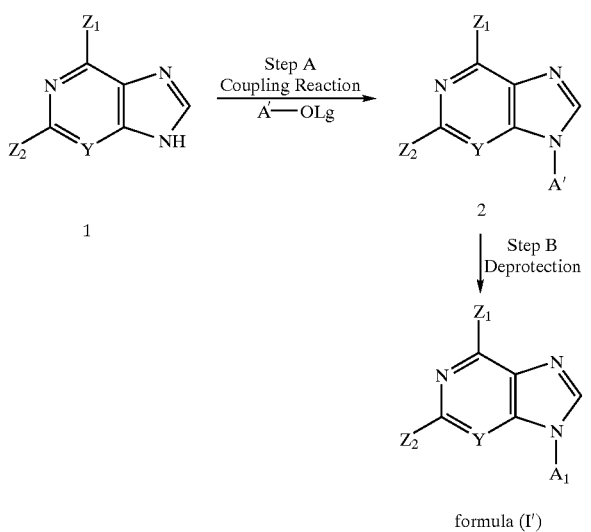

formula (I')

A'-OLg is a suitably protected bicyclic sulfonate derivative which is readily available to one of ordinary skill in the art. A'-OLg is selected from the group consisting of:

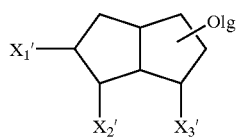
(a')

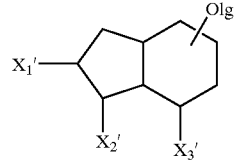
(b')

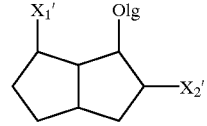
(c')

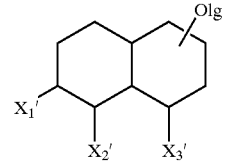
(d')

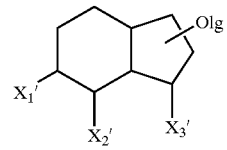
(e')

wherein $X_1'$, $X_2'$ and $X_3'$ are each independently hydrogen or OPg wherein Pg is a suitable protecting group with the proviso that at least one of $X_1'$, $X_2'$ or $X_3'$ is other than hydrogen. Examples of suitable protecting groups are isopropyldimethylsilyl, tert-butyldiphenylsilyl, methyl-di-tert-butylsilyl, tert-butyldimethylsilyl, benzyl, p-methoxybenzyl, o-nitrobenzyl, p-nitrobenzyl, p-chlorobenzyl, triphenylmethyl, methoxymethyl, 2-methoxyethoxymethyl, acetate, benzoate and the like. The preferred protecting group is tert-butyldimethylsilyl.

In Scheme I, step A the bicyclic compound of structure (1) is coupled to the suitably protected sulfonate derivative A'-OLg under conditions well known in the art.

For example, the bicyclic compound (1) is combined with a suitable solvent, such as dimethylformamide in a reaction bomb and treated with an equivalent of a suitable base, such as sodium hydride. Examples of appropriately substituted bicyclic compounds (1) are adenine, 2,6-diaminopurine, 6-chloropurine, 2-amino-6-chloropurine, 3-deazaadenine and the like. Adenine is the preferred bicyclic compound (1). The reaction is allowed to stir for about 1 to 3 hours at room temperature to provide the anion of bicyclic compound (1). About 0.3 to 0.4 equivalents of the suitably protected sulfonate derivative A'-OLg is added to the anion of bicyclic compound (1) in the bomb. The bomb is sealed and heated at about 150° C. for about 10 to 24 hours. After cooling the product is isolated by extractive techniques well known in the art. For example the reaction is rinsed with water, brine, dried over anhydrous sodium sulfate, filtered and concentrated under vacuum. The residue is then purified by techniques well known in the art, such as flash chromatography on silica gel to provide the protected compound described by structure (2).

In Scheme I, step B the protecting group(s) on protected compound (2) is(are) removed under conditions well known in the art that may vary depending upon the particular protecting group utilized to provide the desired deprotected compound described by formula (I') wherein $A_1$ is selected from the group consisting of:

(a) 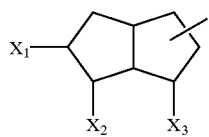

(b) 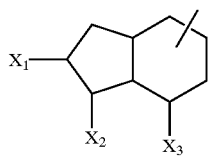

(c) 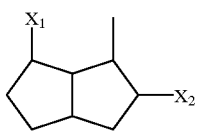

(d) 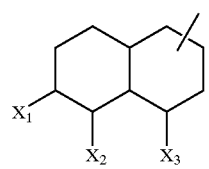

(e) 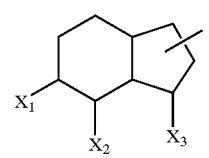

wherein $X_1$, $X_2$ and $X_3$ are each independently hydrogen or OH with the proviso that at least one of $X_1$, $X_2$ or $X_3$ is other than hydrogen. When more than one protecting group is present on compound (2) they may be removed simultaneously or sequentially depending upon the protecting group employed, the reaction conditions utilized and the product desired by techniques well known and understood in the art of chemistry.

In addition compounds of formula (I') can be prepared by treatment of cis-endo-8-hydroxy-bicyclo[3.3.0]octane-endo-2,3-oxirane with the anion of bicyclic compound (1) to provide a mixture of epoxide ring opened products (Ia') and (Ib')

Ia'

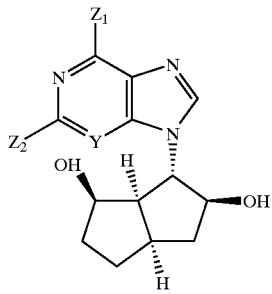

Ib' which can be separated by techniques well known in the art such as flash chromatography on silica gel.

The compounds of formulas (I) and (II) wherein X is $N_3$, NHR, $N(R)_2$, CN, SH or SR can be prepared as described in Scheme II. All other substituents, unless otherwise indicated, are previously defined. Starting material for preparation of compounds of formula (II) can be prepared as described in U.S. Pat. No. 4,479,951, Oct. 30, 1984 and U.S. Pat. No. 4,535,158, Aug. 13, 1985. The reagents and starting materials are readily available to one of ordinary skill in the art.

Scheme II

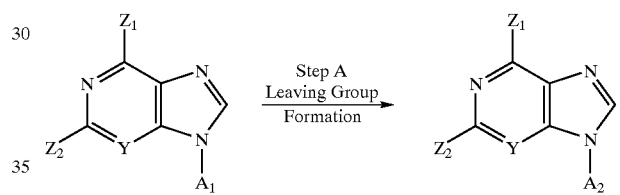

formula (I')
or
formula (III)

Step B
Nucleophilic
Substitution formula (I'')
or
formula (II')

In Scheme II, step A formula (I') or (III) are converted to compound (3) under conditions well known in the art wherein $A_2$ is selected from the group consisting of;

(a)

-continued

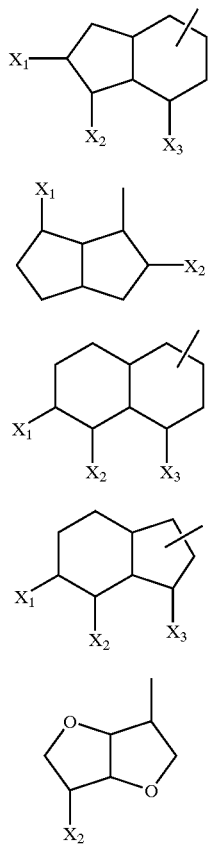

(b)

(c)

(d)

(e)

(f)

wherein $X_1$, $X_2$ and $X_3$ are each independently hydrogen or OLg with the proviso that at least one of $X_1$, $X_2$ or $X_3$ is other than hydrogen. Lg is a suitable leaving group. Examples of suitable leaving groups are methanesulfonate, trifluoromethanesulfonate, p-toluenesulfonate, 2-nitrobenzenesulfonate, 3-nitrobenzenesulfonate, 4-nitrobenzenesulfonate, 4-bromobezenesulfonate and the like. Methanesulfonate is the preferred leaving group.

For example, the appropriately substituted compound of formulas (I') or (III) are dissolved in a suitable organic solvent mixture, such as methylene chloride and tetrahydrofuran (5:3). An excess of methanesulfonyl chloride and triethylamine is added and the reaction is stirred for 30 minutes to 3 hours. The reaction is then quenched with water and extracted with a suitable organic solvent, such as methylene chloride. The combined organic extracts are dried over a suitable drying agent, such as anhydrous sodium sulfate, filtered and concentrated under vacuum to provide the compound described by structure (3).

In Scheme II, step B the compounds described by structure (3) undergo a nucleophilic substitution reaction by treatment with a suitable nucleophile to provide the compounds described by formulas (I'') and (II') wherein $A_3$ is selected from the group consisting of:

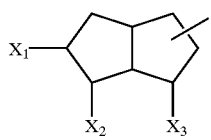

(a)

-continued

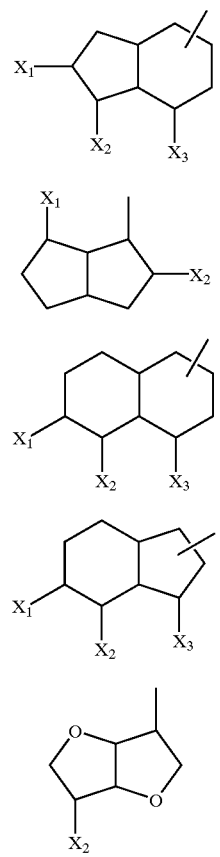

(b)

(c)

(d)

(e)

(f)

wherein $X_1$, $X_2$ and $X_3$ are each independently hydrogen, $N_3$, NHR, $N(R)_2$, CN or SH with the proviso that at least one of $X_1$, $X_2$ or $X_3$ is other than hydrogen.

For example an appropriately substituted compound (3) is dissolved in a suitable solvent. Examples of a suitable solvent are dimethylsulfoxide, dimethylformamide, ethanol and the like. The preferred solvent is ethanol. The solution is then treated with an excess of a suitable nucleophile. Examples of suitable nucleophiles include sodium azide, sodium cyanide, potassium cyanide, lithium cyanide, methylamine, dimethylamine, methyl mercaptide, sodium hydrosulfide, potassium thioacetate and the like. The reaction is stirred at room temperature for approximately 24 hours and then heated at reflux for 2 to 6 hours. Alternatively the reaction can be directly heated at reflux for 2 to 6 hours. The reaction is then concentrated under vacuum and the residue is purified by techniques well known to one skilled in the art. For example, the residue is dissolved in a suitable organic solvent mixture, such as methylene chloride:methanol (9:1) and passed through a plug of silica gel. The filtrate is then concentrated under vacuum to provide the appropriately substituted compound described by formulas (I'') or (II').

The compounds of the formulas (I) and (II) wherein X, $X_1$, $X_2$ and $X_3$ are each independently hydrogen, $CH_2NH_2$, $CO_2H$, $CONH_2$ and $CH_2OH$ with the proviso that at least one of X, $X_1$, $X_2$ or $X_3$ is other than hydrogen, can be prepared by one of ordinary skill in the art from the corresponding cyano substituted derivative of formulas (I'') or (II'), prepared in Scheme II.

For example an appropriately substituted compound of formulas (I'') or (II') wherein $X_1$, $X_2$ and $X_3$ on $A_3$ are each independently hydrogen or CN with the proviso that at least one of $X_1$, $X_2$ or $X_3$ is other than hydrogen, is reduced to the appropriately substituted aminomethyl compound utilizing techniques well known in the art.

For example, the appropriately substituted cyano compound of formulas (I") or (II') is dissolved in a suitable solvent, such as tetrahydrofuran and treated with an excess of a suitable reducing agent, such as 2M aluminum hydride in tetrahydrofuran. The reaction is refluxed for 2 to 6 hours. Excess reducing agent is carefully decomposed by treatment with acetone and then acidified to pH 7. The mixture is then filtered and the filtrate is concentrated under vacuum. The residue is purified by techniques well known to one skilled in the art. For example, the residue is purified by flash chromatography on silica gel with methylene chloride:methanol (17:3) as eluent to provide the appropriately substituted compounds of formulas (I) and (II) wherein X, $X_1$, $X_2$ and $X_3$ on A are each independently hydrogen or $CH_2NH_2$ with the proviso that at least one of X, $X_1$, $X_2$ or $X_3$ is other than hydrogen.

Additionally, an appropriately substituted compound of formulas (I") or (II') wherein $X_1$, $X_2$ and $X_3$ on $A_3$ are each independently hydrogen or CN with the proviso that at least one of $X_1$, $X_2$ or $X_3$ is other than hydrogen, is hydrolyzed to the appropriately substituted amide derivative utilizing techniques well known in the art.

For example, the appropriately substituted cyano compound of formulas (I") or (II') is dissolved in a suitable solvent, such as methanol and treated with an equivalent of a suitable base, such as potassium hydroxide. The reaction is heated at reflux for 1 to 5 hours and then concentrated under vacuum. The residue is then purified by techniques well known in the art. For example the residue can be purified by flash chromatography on silica gel utilizing a suitable eluent, such as methylene chloride:methanol to provide the appropriately substituted compounds of formulas (I) and (II) wherein X, $X_1$, $X_2$ and $X_3$ on A are each independently hydrogen or $CONH_2$ with the proviso that at least one of X, $X_1$, $X_2$ or $X_3$ is other than hydrogen.

Additionally, an appropriately substituted compound of formulas (I") or (II') wherein $X_1$, $X_2$ and $X_3$ on $A_3$ are each independently hydrogen or CN with the proviso that at least one of $X_1$, $X_2$ or $X_3$ is other than hydrogen, is hydrolyzed to the appropriately substituted carboxylic acid derivative utilizing techniques well known in the art.

For example, the appropriately substituted cyano compound of formulas (I") or (II') is dissolved in a suitable organic solvent, such as tetrahydrofuran. An excess of a suitable base, such as potassium hydroxide is added and the reaction is heated at reflux for approximately 6 hours. After cooling, the reaction is neutralized with a suitable acid, such as 6N hydrochloric acid and the product purified by techniques well known to one skilled in the art. For example, the product can be isolated by ion exchange chromatography to provide the appropriately substituted compounds of formulas (I) and (II) wherein X, $X_1$, $X_2$ and $X_3$ on A are each independently hydrogen or $CO_2H$ with the proviso that at least one of X, $X_1$, $X_2$ or $X_3$ is other than hydrogen.

The carboxylic acid derivative described above can then be reduced under conditions well known in the art to provide the corresponding hydroxymethyl derivative.

For example, the appropriately substituted carboxylic acid is dissolved in a suitable organic solvent, such as tetrahydrofuran. An excess of a suitable reducing agent, such as 2M lithium aluminum hydride in tetrahydrofuran is added dropwise to the reaction. The reaction is heated at reflux for 2 to 6 hours. After cooling, excess reducing agent is decomposed by treatment with acetone followed by dilute hydrochloric acid to adjust to pH 7. The mixture is then filtered and the filtrate is concentrated under vacuum. The residue is then purified by techniques well known to one skilled in the art. For example, the residue can be purified by flash chromatography using methylene chloride:methanol (17:3) as the eluent to provide the appropriately substituted compounds of formulas (I) and (II) wherein X, $X_1$, $X_2$ and $X_3$ on A are each independently hydrogen or $CH_2OH$ with the proviso that at least one of X, $X_1$, $X_2$ or $X_3$ is other than hydrogen.

The compounds of the formulas (I) and (II) wherein X, $X_1$, $X_2$ and $X_3$ are on A are hydrogen or $NH_2$ with the proviso that at least one of $X_1$, $X_2$ or $X_3$ is other than hydrogen, can be prepared from the corresponding azide derivative [the azide derivative is prepared by nucleophilic substitution of compound (3) with sodium azide as described generally in Scheme II, step B].

For example, the appropriately substituted azide [formulas (I") or (II') wherein $X_1$, $X_2$, and $X_3$ are each independently hydrogen or $N_3$ with the proviso that at least one of $X_1$, $X_2$ or $X_3$ is other than hydrogen.] is dissolved in a suitable organic solvent, such as tetrahydrofuran and treated with an excess of a suitable reducing agent, such as 2M lithium aluminum hydride in tetrahydrofuran. The reaction is heated at reflux for 2 to 6 hours. After cooling, the excess reducing agent is decomposed with water, the mixture is filtered and the filtrate is concentrated under vacuum. The residue is then purified by techniques well known to one skilled in the art. For example, the residue is purified by flash chromatography using silica gel and a suitable organic eluent, such as methylene chloride:methanol (17:3) to provide the appropriately substituted compounds of formulas (I) and (II) wherein X, $X_1$, $X_2$ and $X_3$ on A are each independently hydrogen or $NH_2$ with the proviso that at least one of $X_1$, $X_2$ or $X_3$ is other than hydrogen.

More specifically the compounds of of formula (I) wherein A is an appropriately substituted octahydropentalene, $X_1$ and $X_3$ are hydrogen, and $X_2$ is OH, can be prepared as described in Scheme III. All the substituents, unless otherwise indicated, are previously defined. The reagents and starting materials are readily available to one of ordinary skill in the art.

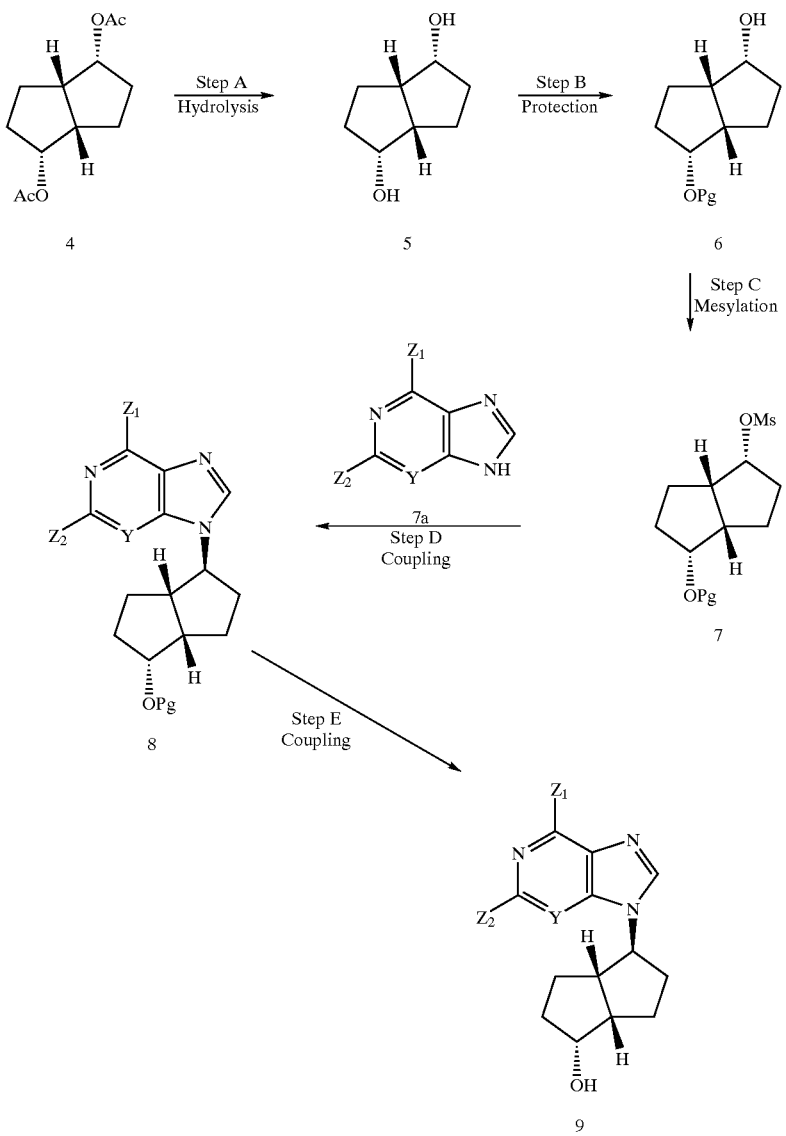

Scheme III

In Scheme III, step A the (+)-diendo-2,6-diacetoxybicyclo [3,3,0]octane (4) [prepared following the procedure described by Henry et al. *J. Chem. Soc. Chem. Comm.* 1974, 112] is hydrolyzed to the dihydroxy derivative described by structure (5).

For example the (+)-diendo-2,6-diacetoxybicyclo[3,3,0] octane (4) is dissolved in a suitable organic solvent, such as methanol and treated with 2 equivalents of a suitable base, such as potassium hydroxide and allowed to stir at room temperature for 1 to 3 hours. The reaction is then concentrated under vacuum and the residue purified by techniques well known in the art, such as chromatography on silica gel to provide the dihydroxy derivative (5).

In step B the dihydroxy derivative (5) is monoprotected under conditions well known in the art to provide the appropriately substituted monohydroxy derivative described by structure (6).

For example the dihydroxy derivative (5) is dissolved in a suitable organic solvent, such as methylene chloride. It is then treated with a catalytic amount of 4-dimethylaminopyridine, an equivalent of a suitable acid scavenger, such as triethylamine and an equivalent of a suitable protecting group. Examples of suitable protecting groups are tert-butyldimethylsilyl, isopropyldimethylsilyl, methyl-di-tert-butylsilyl, tert-butyldimethylsilyl, acetate, benzoate, tetrahydropyranyl and the like. The preferred protecting group is tert-butyldimethylsilyl. The reaction is allowed to stir for 10 to 24 hours at room temperature. The product is then isolated extractive methods well known in the art. For example the reaction can be washed with water, brine, dried over anhydrous sodium sulfate, filtered and concentrated under vacuum. The residue is then purified by techniques well known in the art, such as flash chromatography on silica gel to provide the monohydroxy derivative (6).

In step C the monohydroxy derivative (6) is converted to the appropriately substituted mesylate described by structure (7) under conditions well known in the art.

For example the monohydroxy derivative (6) is dissolved in a suitable organic solvent, such as methylene chloride. It is then treated with a slight excess of methanesulfonyl chloride and a slight excess of a suitable acid scavenger, such as triethylamine. The reaction is stirred for 1 to 3 hours at room temperature. The mesylate (7) is then isolated by extractive methods well known in the art. For example the reaction is washed with water, brine, dried over anhydrous sodium sulfate, filtered and concentrated under vacuum to provide the mesylate (7).

In step D the mesylate (7) is immediately coupled to the appropriately substituted anion of the bicyclic compound of structure (7a) under conditions that are well known in the art to provide the appropriately substituted compound (8).

For example an appropriately substituted bicyclic compound (7a) is combined with a suitable solvent, such as dimethylformamide in a reaction bomb and then treated with an equivalent of a suitable base, such as sodium hydride. Examples of bicyclic compounds (7a) are adenine, 2,6-diaminopurine, 6-chloropurine, 2-amino-6-chloropurine, 3-deazoadenine and the like. The preferred bicyclic compound (7a) is adenine. The reaction is allowed to stir for about 1 to 3 hours at room temperature to provide the anion of (7a). About 0.3 to 0.4 equivalents of the mesylate (7) are added to the anion of (7a) in the bomb, the bomb is sealed and heated at about 150° C. for about 10 to 24 hours. After cooling the product is isolated by extractive techniques well known in the art. For example the reaction is rinsed with water, brine, dried over anhydrous sodium sulfate, filtered and concentrated under vacuum. The residue is then purified by techniques well known in the art, such as flash chromatography on silica gel to provide compound (8).

In step E the protecting group on compound (8) is removed under conditions well known in the art that may vary depending upon the particular protecting group utilized to provide the desired deprotected compound described by structure (9).

For example the appropriately substituted compound (8) wherein Pg is an acid sensitive protecting group such as tert-butyldimethylsilyl group, is dissolved in a suitable solvent mixture, such as methanol and water in about a one to one ratio and then treated with 6N hydrochloric acid until the pH of the reaction is about 2. The reaction is allowed to stir for about 2 to 6 hours and is then concentrated under vacuum to provide the desired deprotected compound (9).

More specifically, the compounds of the formulas (I) and (II) wherein A is an appropriately substituted 5—5 bicyclic ring system, $X_1$ and $X_3$ are hydrogen, and $X_2$ or X is $CH_2NH_2$, $CO_2H$, $CONH_2$ or $CH_2OH$ can be prepared as described in Scheme IV. All other substituents, unless otherwise indicated, are previously defined. The reagents and starting materials are readily available to one of ordinary skill in the art.

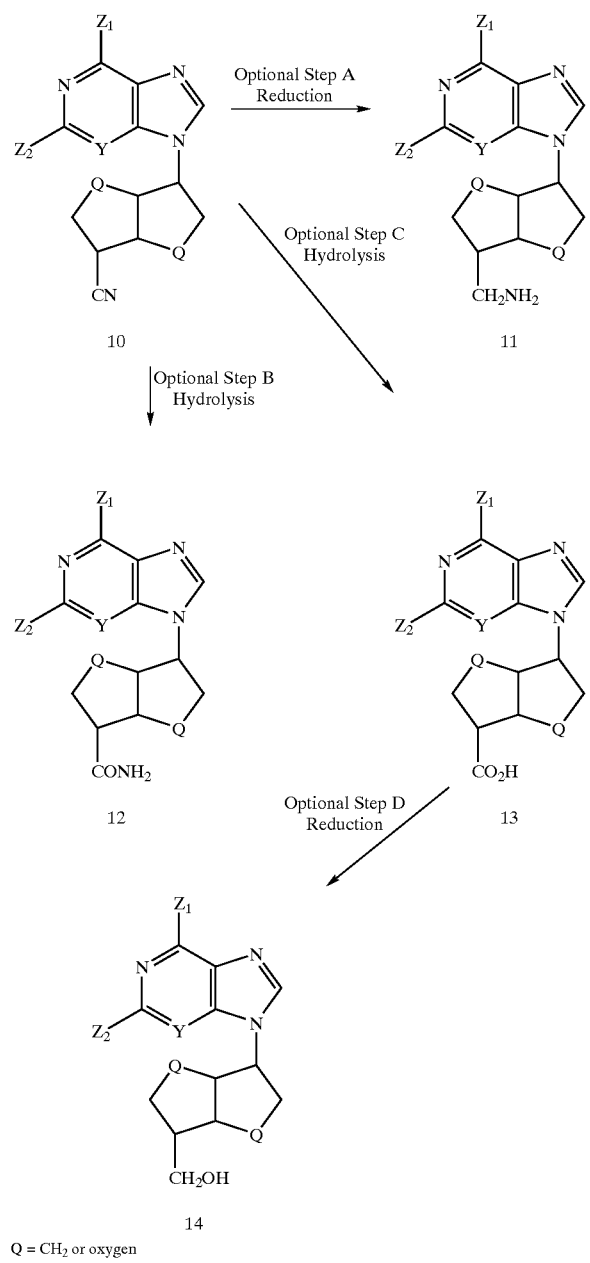

Scheme IV

Q = $CH_2$ or oxygen

For example, in Scheme IV, step A the cyano derivative described by structure (10) [prepared by nucleophilic substitution of the appropriately substituted derivative of compound (3) with potassium cyanide as described generally in Scheme II, step B] is reduced to the appropriately substituted aminomethyl compound described by structure (11).

For example, an appropriately substituted cyano compound described by structure (10) is dissolved in a suitable solvent, such as tetrahydrofuran and treated with an excess of a suitable reducing agent, such as 2M aluminum hydride in tetrahydrofuran. The reaction is refluxed for 2 to 6 hours. Excess reducing agent is carefully decomposed by treatment with acetone and then acidified to pH 7. The mixture is then filtered and the filtrate is concentrated under vacuum. The residue is purified by techniques well known to one skilled in the art. For example, the residue is purified by flash chromatography on silica gel with methylene chloride:methanol (17:3) as eluent to provide the aminomethyl compound described by structure (11).

In Scheme IV, step B the appropriately substituted cyano compound described by structure (10) is hydrolyzed to the appropriately substituted amide described by structure (12).

For example, an appropriately substituted cyano compound described by structure (10) is dissolved in a suitable solvent, such as methanol and treated with an equivalent of a suitable base, such as potassium hydroxide. The reaction is heated at reflux for 1 to 5 hours and then concentrated under vacuum. The residue is then purified by techniques well known in the art. For example the residue can be purified by flash chromatography on silica gel utilizing a suitable eluent, such as methylene chloride:methanol to provide the purified amide (12).

In Scheme IV, optional step C the appropriately substituted cyano compound described by structure (12) is hydrolyzed to the appropriately substituted carboxylic acid described by structure (13).

For example, an appropriately substituted cyano compound described by structure (10) is dissolved in a suitable organic solvent, such as tetrahydrofuran. An excess of a suitable base, such as potassium hydroxide is added and the reaction is heated at reflux for approximately 6 hours. After cooling, the reaction is neutralized with a suitable acid, such as 6N hydrochloric acid and the product purified by techniques well known to one skilled in the art. For example, the product can be isolated by ion exchange chromatography to provide the carboxylic acid described by structure (13).

In Scheme IV, step D the appropriately substituted carboxylic acid described by structure (13) is reduced to the appropriately substituted alcohol described by structure (14).

For example, an appropriately substituted carboxylic acid described by structure (13) is dissolved in a suitable organic solvent, such as tetrahydrofuran. An excess of a suitable reducing agent, such as 2M lithium aluminum hydride in tetrahydrofuran is added dropwise to the reaction. The reaction is heated at reflux for 2 to 6 hours. After cooling, excess reducing agent is decomposed by treatment with acetone followed by dilute hydrochloric acid to adjust to pH 7. The mixture is then filtered and the filtrate is concentrated under vacuum. The residue is then purified by techniques well known to one skilled in the art. For example, the residue can be purified by flash chromatography using methylene chloride:methanol (17:3) as the eluent to provide the hydroxymethyl derivative described by structure (14).

The compounds of the formulas (I) and (II) wherein A is an appropriately substituted 5—5 bicyclic ring system, $X_1$ and $X_3$ are hydrogen, and X or $X_2$ is $NH_2$ can be prepared as described in Scheme V. All other substituents, unless otherwise indicated, are previously defined. The reagents and starting materials are readily available to one of ordinary skill in the art.

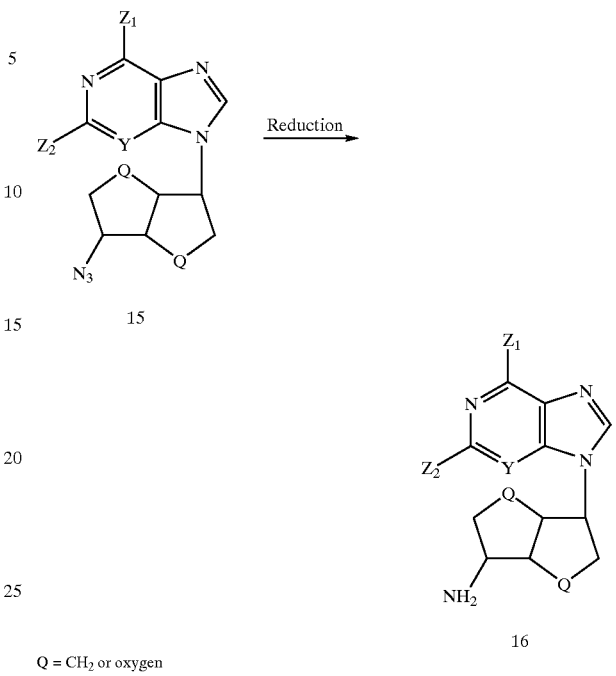

Scheme V

Q = $CH_2$ or oxygen

In Scheme V, the appropriately substituted azide [prepared by nucleophilic substitution of sodium azide on compound (3) as described generally in Scheme II, step B] described by structure (15) is reduced to the appropriately substituted primary amine described by structure (16).

For example, an appropriately substituted azide (15) is dissolved in a suitable organic solvent, such as tetrahydrofuran and treated with an excess of a suitable reducing agent, such as 2M lithium aluminum hydride in tetrahydrofuran. The reaction is heated at reflux for 2 to 6 hours. After cooling, the excess reducing agent is decomposed with water, the mixture is filtered and the filtrate is concentrated under vacuum. The residue is then purified by techniques well known to one skilled in the art. For example, the residue is purified by flash chromatography using silica gel and a suitable organic eluent, such as methylene chloride:methanol (17:3) to provide the appropriately substituted primary amine described by structure (16).

The compounds of formula (III) can be prepared following the procedure described by Klessing and Chatterjee in U.S. Pat. No. 4,479,951, Oct. 30, 1984 and by Klessing, K. in U.S. Pat. No. 4,535,158, Aug. 13, 1985 the disclosure of which are hereby incorporated by reference.

The relative configurations encompassed by the stereoisomers of formulas (I), (II) and (III) are readily prepared by one skilled in the art. In addition the enantiomers of formulas (I), (II) and (III) can be resolved utilizing techniques well known in the art of chemistry such as crystallization techniques described by Jacques, J. et al. "Enantiomers, Racemates, and Resolutions", John Wiley and Sons, Inc., 1981 or by chiral column chromatography.

The following examples present typical syntheses as described by Schemes I, II, III, IV and V. These examples are understood to be illustrative only and are not intended to Limit the scope of the invention in any way. As used in the following examples, the following terms have the meanings indicated: "eq." refers to equivalents, "g" refers to grams, "mg" refers to milligrams, "mmol" refers to millimoles, "mL" refers to milliliters, "° C." refers to degrees Celsius, "δ" refers to ppm downfield from tetramethylsilane, "Pg" refers to a protecting group, "TLC" refers to thin layer chromatography and "$R_f$" refers to retention factor.

EXAMPLE 1

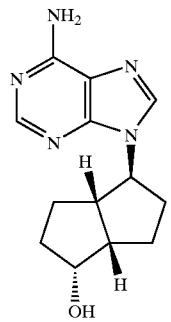

Preparation of the Final Product, (±)-Exo-2-adenyl-endo-6-hydroxybicyclo[3,3,0]octane Dihydrochloride Scheme III, Step A;
Preparation of (±)-Diendo-2,6-dihydroxybicyclo[3,3,0]octane.

Dissolve (±)-diendo-2,6-diacetoxybicyclo[3,3,0]octane (1.5 g, 6.6 mmol) in methanol (60 mL) and add potassium hydroxide (0.53 g, 13.2 mmol). Stir the reaction for 1 hours at room temperature. Concentrate the reaction under vacuum and dissolve the residue in methylene chloride. Filter the solution and dilute with methylene chloride/ethyl acetate (1:1). Pass the solution through a plug of silica gel and concentrate the collected eluent under vacuum to provide the title compound (730 mg).

Scheme III, Step B;

Preparation of (±)-Diendo-6-t-butyldimethylsilyloxy-2-hydroxybicyclo[3,3,0]octane Dissolve (±)-diendo-2,6-dihydroxybicyclo[3,3,0]octane (0.73 g, 5.1 mmol) in methylene chloride (50 mL) and add tert-butyldimethylsilyl chloride (0.77 g, 5.1 mmol), 4-dimethylaminopyridine (10 mg) and triethylamine (0.52 g, 5.1 mmol). Stir the reaction overnight. Wash the reaction with water, brine, dry over anhydrous sodium sulfate, filter and concentrate under vacuum to provide an oil. Purify the crude oil by flash chromatography (hexane/ethyl acetate, 3:2, silica gel) to provide the title compound (1.07 g).

Scheme III, Steps C and D;

Preparation of (±)-Exo-2-adenyl-endo-6-t-butyldimethylsilyloxybicyclo[3,3,0]octane Dissolve (±)-Diendo-6-t-butyldimethylsilyloxy-2-hydroxybicyclo[3,3,0]octane (0.9 g, 3.5 mmol) in methylene chloride (30 mL). Add methanesulfonyl chloride (0.48 g, 4.2 mmol), triethylamine (0.42 g, 4.2 mmol) and stir for one hour. Rinse the reaction with water, brine, dry over anhydrous sodium sulfate, filter and concentrate to yield the mesylate as a yellow oil. This mesylate is then immediately added to a reaction bomb containing a solution of sodium adenide in dimethylformamide, [prepared by treating adenine (1.43 g, 10.5 mmol) in dimethylformamide (30 mL) with sodium hydride (0.42 g of a 60% dispersion, 10.5 mmol) and stirring for 1.25 hours at room temperature]. Seal the reaction bomb and heat at 150° C. overnight. Then transfer the reaction mixture to a round bottom flask and concentrate under vacuum. Dissolve the residue in methylene chloride, rinse with water, brine, dry over anhydrous sodium sulfate, filter and concentrate under vacuum. Purify the residue by flash chromatography (methylene chloride/ethanol, 9:1, silica gel) to provide the title compound (260 mg).

Scheme III, step E; Dissolve (±)-Exo-2-adenyl-endo-6-t-butyldimethylsilyloxybicyclo[3,3,0]octane (240 mg, 0.6 mmol) in methanol (50 mL) and water (50 mL). Add 6N hydrochloric acid until the pH=2. Stir the reaction for 3 hours at room temperature and then concentrate under vacuum to provide the title compound (210 mg); $^1$H NMR (DMSO-$d_6$) δ 8.7 (s, 1H), 8.55 (s, 1H), 4.55 (q, 1H), 4.0 (q, 1H), 2.8 (m, 1H), 2.7 (m, 1H), 2.15 (m, 2H), 1.95 (m, 1H), 1.8–1.45 (m, 6H).

EXAMPLE 2

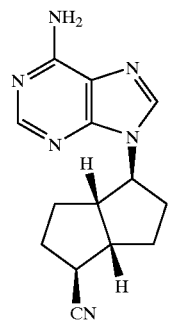

Preparation of (±)-Diexo-2-adenyl-6-cyanobicyclo[3,3,0]octane

Scheme II, step A; Dissolve (±)-Exo-2-adenyl-endo-6-hydroxybicyclo[3,3,0]octane (0.7 mmol) in methylene chloride (15 mL) and tetrahydrofuran (9 mL). Add excess methanesulfonyl chloride and triethylamine and stir for 30 minutes. Add water (50 mL) and separate the layers. Extract the aqueous phase with methylene chloride (50 mL), combine the organic phases and dry over anhydrous sodium sulfate. Filter and concentrate to provide (±)-exo-2-adenyl-endo-6-methanesulfoxybicyclo[3,3,0]octane.

Scheme II, step B; Dissolve (±)-exo-2-adenyl-endo-6-methanesulfoxybicyclo[3,3,0]octane (0.6 mmol) and potassium cyanide (1.2 mmol) in dimethylsulfoxide. Heat the reaction at 75° C. for 6 hours and then concentrate under vacuum. Purify the residue by dissolving it in a mixture of methylene chloride:methanol (9:1) and then passing the solution through a silica gel plug. Concentrate the filtrate under vacuum to provide the title compound.

EXAMPLE 3

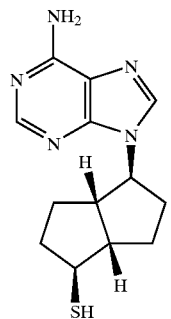

Preparation of (±)-Diexo-2-adenyl-bicyclo[3,3,0]
octane-6-thiol

Scheme II, step B; Dissolve (±)-exo-2-adenyl-endo-6-methanesulfoxybicyclo[3,3,0]octane (0.6 mmol, prepared in example 2) and sodium hydrogensulfide (1.2 mmol) in ethanol. Reflux the reaction for three hours and then concentrate under vacuum. Purify the residue by dissolving it in a mixture of methylene chloride:methanol (9:1) and then pass the solution through a silica gel plug. Concentrate the filtrate under vacuum to provide the title compound.

EXAMPLE 4

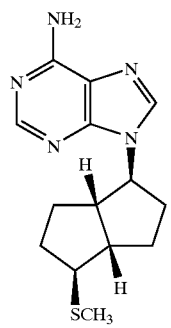

Preparation of (±)-Diexo-2-adenyl-6-methylmercaptobicyclo[3,3,0]octane

Scheme II, step B; Combine (±)-exo-2-adenyl-endo-6-methanesulfoxybicyclo[3,3,0]octane (0.6 mmol, prepared in example 2) and potassium hydroxide (1.2 mmol) in methanol. Bubble in methyl mercaptan until the solution is saturated and then reflux for three hours. Concentrate the reaction under vacuum. Purify the residue by dissolving it in a mixture of methylene chloride:methanol (9:1) and then pass the solution through a silica gel plug. Concentrate the filtrate under vacuum to provide the title compound.

EXAMPLE 5

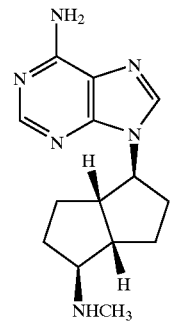

Preparation of (±)-Diexo-2-adenyl-6-methylaminobicyclo[3,3,0]octane

Scheme II, step B; Dissolve (±)-exo-2-adenyl-endo-6-methanesulfoxybicyclo[3,3,0]octane (0.6 mmol, prepared in example 2) and methylamine (1.2 mmol) in ethanol. Reflux the reaction for three hours and then concentrate under vacuum. Purify the residue by dissolving it in a mixture of methylene chloride:methanol (9:1) and then pass the solution through a silica gel plug. Concentrate the filtrate under vacuum to provide the title compound.

EXAMPLE 6

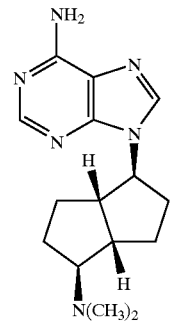

Preparation of (±)-Diexo-2-adenyl-6-dimethylaminobicyclo[3,3,0]octane

Scheme II, step B; Dissolve 1R,3S-cis-1-(9-adenyl)-3-methanesulfoxycyclopentane (0.6 mmol, prepared in example 2) and dimethylamine (1.2 mmol) in ethanol. Reflux the reaction for three hours and then concentrate under vacuum. Purify the residue by dissolving it in a mixture of methylene chloride:methanol (9:1) and then pass the solution through a silica gel plug. Concentrate the filtrate under vacuum to provide the title compound.

EXAMPLE 7

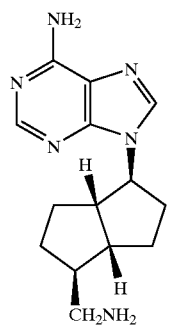

Preparation of (±)-Diexo-2-adenyl-6-aminomethylbicyclo[3,3,0]octane

Scheme IV, optional step A; Dissolve (±)-Diexo-2-adenyl-6-cyanobicyclo[3,3,0]octane (prepared in example 2) in tetrahydrofuran and add excess 2M lithium aluminum hydride in tetrahydrofuran dropwise. Reflux for two to six hours. Decompose the excess lithium aluminum hydride, filter and concentrate under vacuum. Purify the residue by flash chromatography (silica gel) using methylene chloride:methanol (17:3) as the eluent to provide the title compound.

EXAMPLE 8

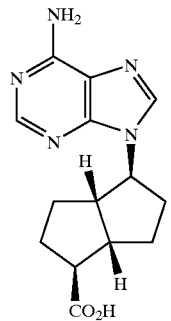

Preparation of (±)-Diexo-2-adenyl-bicyclo[3,3,0] octane-6-carboxylic Acid

Scheme IV, optional step C; Dissolve (±)-Diexo-2-adenyl-6-cyanobicyclo[3,3,0]octane (prepared in example 2) in tetrahydrofuran and add excess potassium hydroxide. Reflux for approximately 6 hours. Neutralize the reaction with 6N hydrochloric acid and purify by ionexchange chromatography to provide the title compound.

EXAMPLE 8b

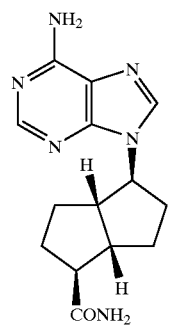

Preparation of (±)-Diexo-2-adenyl-bicyclo[3,3,0] octane-6-carboxamide

Scheme IV, optional step B; Dissolve (±)-Diexo-2-adenyl-6-cyanobicyclo[3,3,0]octane (1 mmol, prepared in example 2) in methanol and treat with potassium hydroxide (1 mmol). Heat the reaction at reflux for 2 hours. After cooling concentrate under vacuum and purify the residue by flash chromatography (methylene chloride/methanol, 17:3, silica gel) to provide the title compound.

EXAMPLE 9

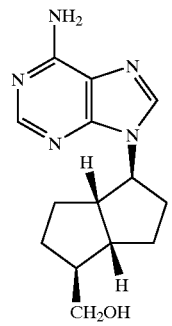

Preparation of (±)-Diexo-2-adenyl-6-hydroxymethylbicyclo[3,3,0]octane

Scheme IV, optional step D; Dissolve (±)-Diexo-2-adenyl-bicyclo[3,3,0]octane-6-carboxylic acid (prepared in example 8) in tetrahydrofuran and add excess 2M lithium aluminum hydride in tetrahydrofuran dropwise. Reflux for two to six hours. Decompose the excess lithium aluminum hydride, filter, concentrate under vacuum and purify in a manner analogous to example 9 to provide the title compound.

EXAMPLE 10

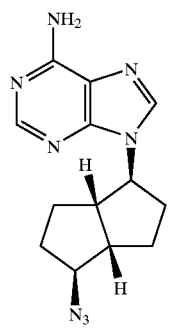

Preparation of (±)-Diexo-2-adenyl-6-azidobicyclo[3,3,0]octane

Scheme I, step B; Dissolve (±)-exo-2-adenyl-endo-6-methanesulfoxybicyclo[3,3,0]octane (0.6 mmol, prepared in example 2) and lithium azide (60 mg, 1.2 mmol) in ethanol (10 mL). Stir overnight at room temperature and then reflux for three hours. Concentrate the reaction under vacuum and purify the residue by dissolving it in a mixture of methylene chloride:methanol (9:1) and then pass the solution through a silica gel plug. Concentrate the filtrate under vacuum to provide the title compound.

EXAMPLE 11

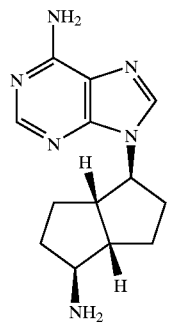

Preparation of (±)-Diexo-2-adenyl-6-aminobicyclo[3,3,0]octane Dihydrochloride

Scheme V; Dissolve (±)-Diexo-2-adenyl-6-azidobicyclo[3,3,0]octane (prepared in example 10) in tetrahydrofuran and add excess 2M lithium aluminum hydride in tetrahydrofuran dropwise. Reflux for two to six hours. Decompose the excess lithium aluminum hydride, filter and concentrate under vacuum. Purify the residue by dissolving it in a mixture of methylene chloride;methanol (9:1) and then pass the solution through a silica gel plug. Concentrate the filtrate under vacuum to provide the title compound.

EXAMPLE 12

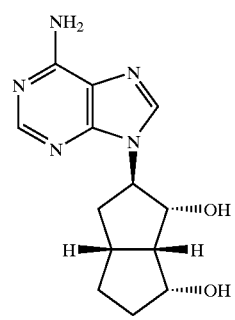 (A)

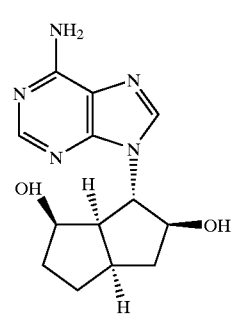 (B)

Preparation of (±)-Exo-5-(6-amino-purin-9yl)-octahydro-pentalene-diendo-1,6-diol (A) and (±)-Exo-3-(6-amino-purin-9yl)-octahydro-pentalene-diendo-2,5-diol (B)

Add cis-endo-8-hydroxy bicyclo[3.3.0]octane-endo-2,3-oxirane (760 mg, 5.4 mmol, prepared according to Shihusaki, M. et al. *Tet. Lett.* 433, 1979) to a reaction bomb containing a solution of sodium adenide in dimethylformamide, [prepared by treating adenine with an equivalent of sodium hydride in dimethylformamide] and stir at room temperature for 45 minutes. Then seal the bomb and heat overnight at 150° C. to 155° C. Concentrate the reaction under vacuum and purify the residue by flash chromatography on silica gel (methylene chloride/methanol, 9:1) to provide (A) (180 mg) and (B) (240 mg).

EXAMPLE 13

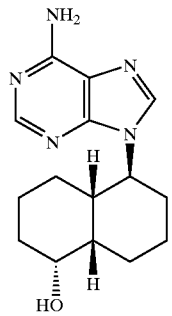

Preparation of (±)-Exo-5-(6-amino-purin-9-yl)-cis-decahydro-naphthalene-endo-1-ol Scheme III; In an analogous manner to Example 1 the title compound is prepared from (±)-diendo-1,5-diacetoxydecalin.

EXAMPLE 14

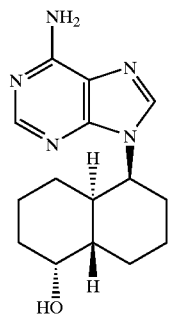

Preparation of (±)-Exo-5-(6-amino-purin-9-yl)-trans-decahydro-naphthalene-endo-1-ol.

Scheme III; In an analogous manner to Example 1 the title compound is prepared from Trans-1,5-diacetoxy-Cis-decalin.

EXAMPLE 14

Preparation of [3S,6R]-6-(6-Amino-purin-9-yl)-hexahydro-furo-[3,2-b]-furan-3-carbonitrile Scheme II, step B; In an analogous manner to Example 2 the title compound is prepared from the methanesulfonate derivative of 6-(6-amino-purin-9-yl)-hexahydro-furo[3,2-b]furan-3-ol.

EXAMPLE 15

Preparation of [3S,6R]-6-(6-Amino-purin-9-yl)-hexahydro-furo[3,2-b]-furan-3-thiol Scheme II, step B; In an analogous manner to Example 3 the title compound is prepared from the methanesulfonate derivative of 6-(6-amino-purin-9-yl)-hexahydro-furo[3,2-b]furan-3-ol.

EXAMPLE 16

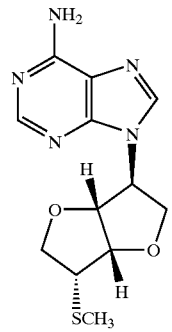

Preparation of [3R, 6S]-9-(6-Methylsulfanyl-hexahydro-furo[3,2-b]-furan-3-yl)-9H-purin-6-ylamine Scheme II, step B; In an analogous manner to Example 4 the title compound is prepared from the methanesulfonate derivative of 6-(6-amino-purin-9-yl)-hexahydro-furo[3,2-b]furan-3-ol.

EXAMPLE 17

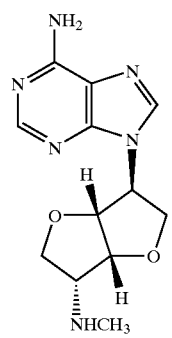

Preparation of [3R, 6S]-9-(6-Methylamino-hexahydro-furo[3,2-b]-furan-3-yl)-9H-purin-6-ylamine Scheme II, step B; In an analogous manner to Example 5 the title compound is prepared from the methanesulfonate derivative of 6-(6-amino-purin-9-yl)-hexahydro-furo[3,2-b]furan-3-ol.

EXAMPLE 18

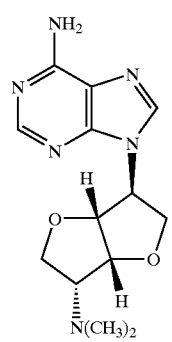

Preparation of [3R, 6S]-9-(6-Dimethylamino-hexahydro-furo[3,2-b]-furan-3-yl)-9H-purin-6-ylamine Scheme II, step B; In an analogous manner to Example 6 the title compound is prepared from the methanesulfonate derivative of 6-(6-amino-purin-9-yl)-hexahydro-furo[3,2-b]furan-3-ol.

EXAMPLE 19

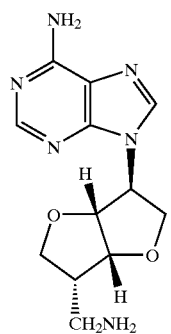

Preparation of [3R, 6S]-9-(6-Aminoemethyl-hexahydro-furo[3,2-b]-furan-3-yl)-9H-purin-6-ylamine Scheme IV, optional step A; In an analogous manner to Example 7 the title compound is prepared from the product prepared in example 14.

EXAMPLE 20

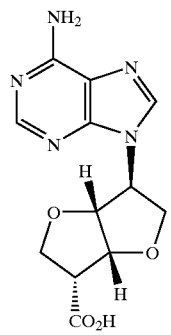

Preparation of [3S, 6R]-6-(6-Amino-purin-9-yl)-hexahydro-furo-[3,2-b]-furan-3-carboxylic Acid Scheme IV, optional step C; In an analogous manner to Example 8 the title compound is prepared from the product prepared in example 14.

EXAMPLE 21

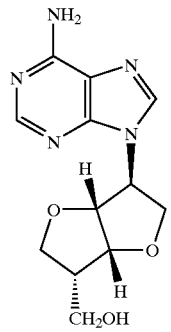

Preparation of [3S, 6R]-[6-(6-Amino-purin-9-yl)-hexahydro-furo-[3,2-b]furan-3-yl]-methanol Scheme IV, optional step D; In an analogous manner to Example 9 the title compound is prepared from the product prepared in example 20.

EXAMPLE 22

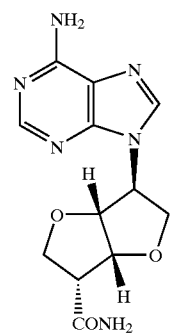

Preparation of [3S, 6R]-6-(6-Amino-purin-9-yl)-hexahydro-furo-[3,2-b]furan-3-carboxylic Acid Amide Scheme IV, optional step B; In an analogous manner to Example 8b the title compound is prepared from the product prepared in example 16.

EXAMPLE 23

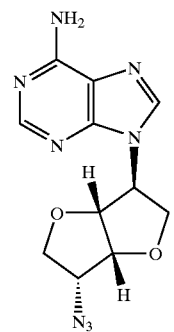

Preparation of [3R, 6S]-9-(6-azido-hexahydro-furo[3,2-b]furan-3-yl)-9H-purin-6-ylamine Scheme II, step B; In an analogous manner to Example 10 the title compound is prepared from the methanesulfonate derivative of 6-(6-amino-purin-9-yl)-hexahydro-furo[3,2-b]furan-3-ol.

EXAMPLE 24

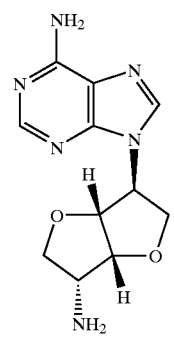

Preparation of [3R, 6S]-9-(6-Amino-hexahydro-furo[3,2-b]furan-3yl)-9H-purin-6-ylamine Scheme V; In an analogous manner to Example 11 the title compound is prepared from the product prepared in example 23.

It is to be noted that the following more specific compounds of formula (I) are readily prepared by applying the foregoing described techniques and procedures and by applying known prior art principles to achieve the necessary modifications:

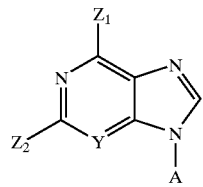

formula (I)

wherein Y is —N—, $Z_1$ is $NH_2$, $Z_2$ is H, and A is selected from the group consisting of;

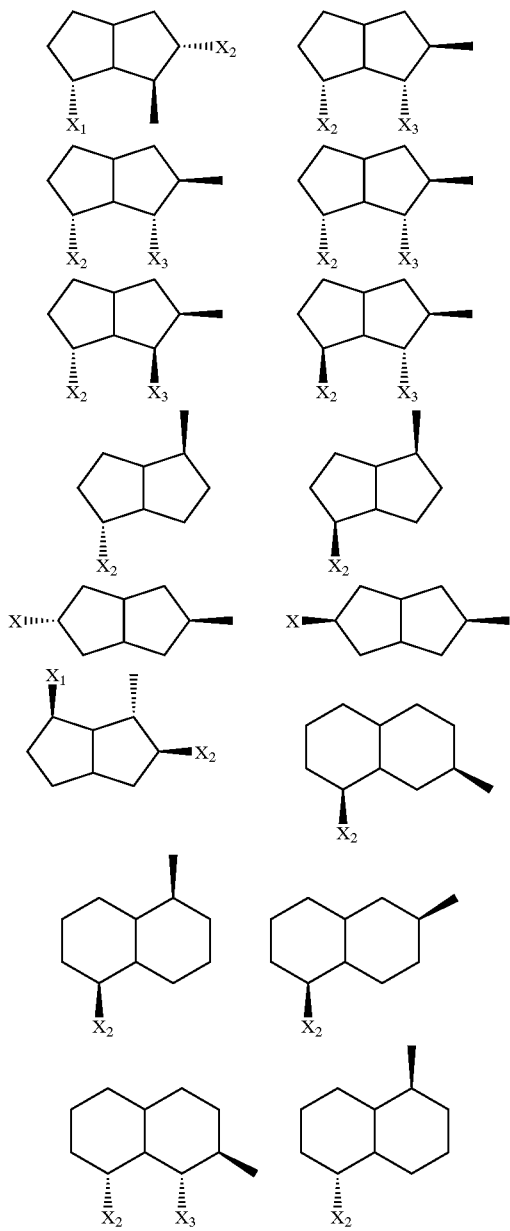

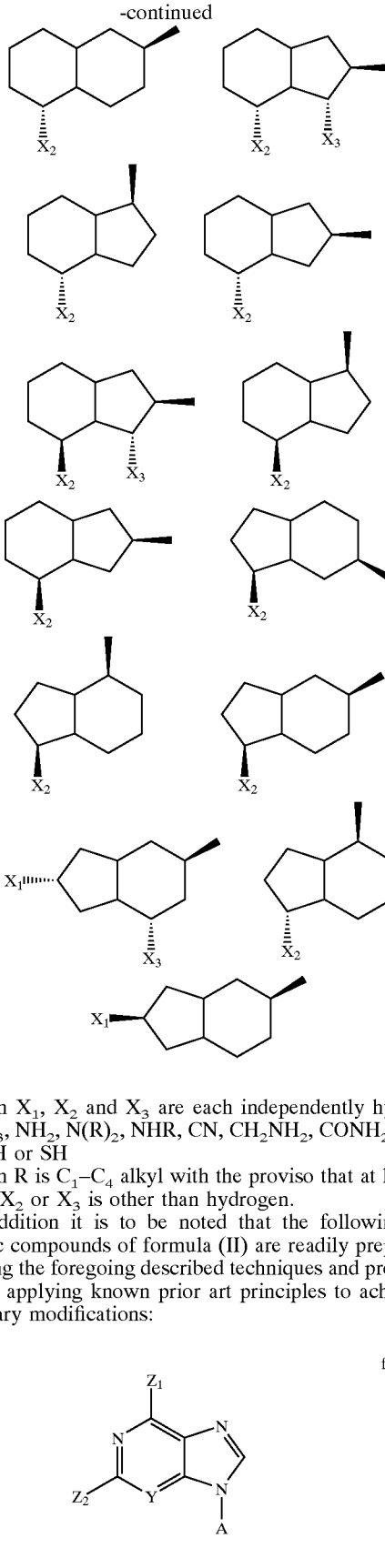

wherein $X_1$, $X_2$ and $X_3$ are each independently hydrogen, OH, $N_3$, $NH_2$, $N(R)_2$, NHR, CN, $CH_2NH_2$, $CONH_2$, $CO_2H$, $CH_2OH$ or SH
wherein R is $C_1$–$C_4$ alkyl with the proviso that at least one of $X_1$, $X_2$ or $X_3$ is other than hydrogen.

In addition it is to be noted that the following more specific compounds of formula (II) are readily prepared by applying the foregoing described techniques and procedures and by applying known prior art principles to achieve the necessary modifications:

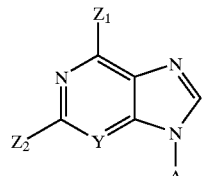

formula (II)

wherein Y is —N—, $Z_1$ is $NH_2$, $Z_2$ is H, and A is selected from the group consisting of;

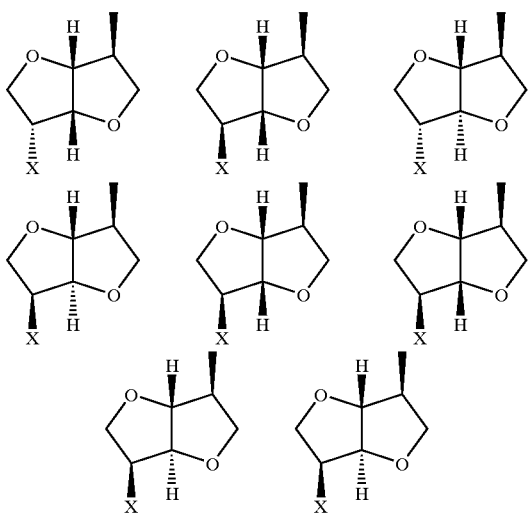

wherein X is $N_3$, $NH_2$, $N(R)_2$, NHR, CN, $CH_2NH_2$, $CONH_2$, $CO_2H$, $CH_2OH$, SH wherein R is $C_1$-$C_4$ alkyl.

The present invention further provides a method of inhibiting TNF-α activity in a patient in need thereof comprising administering to said patient an antiinflammatory amount of a compound of formulas (I), (II) or (III). The present invention further provides a method of treating a patient suffering from certain autoimmune or other diseases for which elevated activity of TNF-α is implicated as a contributing factor in the progression of the disease comprising administering to said patient a compound of formulas (I), (II) or (III).

As used herein, the term "patient" refers to a warm-blooded animal such as a mammal which is suffering from, or is in danger of suffering from, an acute or chronic inflammation, cellular injury or cell death associated with an immunological based disease. It is understood that humans, mice and rats are included within the scope of the term "patient".

Administration of a compound of formulas (I), (II) or (III) to a patient results in a selective antiinflammatory effect in the patient. More specifically, administration of a compound of formulas (I), (II) or (III) to a patient results in inhibition of TNF-α activity in the patient which selectively inhibits TNF-α-mediated inflammatory events. In other words, by treatment of a patient with a compound of formulas (I), (II) or (III), the TNF-α-mediated inflammatory response and subsequent inhibition of other cytokines associated with various diseases is inhibited or suppressed over that present in the absence of treatment.

A patient is in need of treatment with an agent which inhibits TNF-α activity, such as a compound of formulas (I), (II) or (III), where the patient is suffering from certain autoimmune or other diseases for which elevated activity of TNF-α is implicated as a contributing factor in the progression of the disease. The term "autoimmune disease" refers to those disease states and conditions wherein the immune response of the patient is directed against the patient's own constituents resulting in an undesirable and often terribly debilitating condition.

Patients suffering from autoimmune diseases such as septic shock, ARDS, inflammatory bowel disease including ulcerative colitis and Chrohn's disease, rheumatoid arthritis, fever/cachexia (wasting syndrome)/*Myobacterium tuberculosis* infections in patients with AIDS, diabetes mellitus type I, Kawasaki disease, multiple sclerosis,familial Mediterranean fever, toxic shock syndrome are in need of treatment with a selective antiinflammatory agent such as a compound of formulas (I), (II) or (III). In addition, patients suffering from bacterial meningitis, vascular injury/atherosclerosis, leprosy, anemia of chronic disease, ultraviolet radiation, *Helicobacter pylori* gastritis/ulcer disease, paracoccidioidomycosis, septic melioidosis, heart failure, chronic fatigue syndrome, allograft rejection, Graft-versus-host disease, Schistosomiasis are also in need of treatment with a selective antiinflammatory agent such as a compound of formulas (I), (II) or (III). As such, treatment of patients suffering from these diseases by administration of a compound of formulas (I), (II) or (III) will be particularly effective in preventing further deterioration or worsening of the patient's condition. Treatment of a patient at an early stage of an autoimmune disease would be particularly effective in preventing further deterioration of the disease state into a more serious condition.

Patients suffering from septic shock, ARDS, AIDS, fever/cachexia/*Myobacterium tuberculosis* infection associated with AIDS, inflammatory bowel disease including ulcerative colitis and Chrohn's disease, bacterial meningitis, and rheumatoid arthritis are particularly good candidates for treatment with a compound of formulas (I), (II) or (III).

Based on standard clinical and laboratory tests and procedures, an attending diagnostician, as a person skilled in the art, can readily identify those patients who are in need of treatment with a selective antiinflammatory agent such as a compound of formulas (I), (II) or (III).

An effective antiinflammatory amount of a compound of formulas (I), (II) or (III) is that amount which is effective, upon single or multiple dose administration to a patient, in providing an antiinflammatory effect or, more particularly, an inhibition of TNF-α activity. An antiinflammatory effect refers to the slowing, interrupting, inhibiting or preventing the further expression of TNF-α-mediated inflammatory effects.

An effective antiinflammatory amount of a compound of formulas (I), (II) or (III) can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

An effective antiinflammatory amount of a compound of formulas (I), (II) or (III) is expected to vary from about 0.1 milligram per kilogram of body weight per day (mg/kg/day) to about 500 mg/kg/day. Preferred amounts are expected to vary from about 1 to about 50 mg/kg/day.

In effecting treatment of a patient, a compound of formulas (I), (II) or (III) can be administered in any form or mode which makes the compound bioavailable in effective amounts, including oral and parenteral routes. For example, compounds of formulas (I), (II) or (III) can be administered orally, subcutaneously, intramuscularly, intravenously, transdermally, intranasally, rectally, and the like. Oral administration and intravenous administration are generally preferred. One skilled in the art of preparing formulations can readily select the proper form and mode of administration depending upon the particular characteristics of the compound selected the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

In another embodiment, the present invention provides compositions comprising a compound of formulas (I), (II) or (III) in admixture or otherwise in association with one or more inert carriers. These compositions are useful, for example, as assay standards, as convenient means of making bulk shipments, or as pharmaceutical compositions. An assayable amount of a compound of formulas (I), (II) or (III) is an amount which is readily measurable by standard assay procedures and techniques as are well known and appreciated by those skilled in the art. Assayable amounts of a compound of formulas (I), (II) or (III) will generally vary from about 0.001% to about 75% of the composition by weight. Inert carriers can be any material which does not degrade or otherwise covalently react with a compound of formulas (I), (II) or (III). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective immunosuppressive amount of a compound of formula (I), (II) or (III) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use, including topical use, and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, including topical administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possesses a particular generic utility, certain groups and configurations are preferred for compounds of formula (I) in their end-use application. Compounds of the formula (I) wherein Y is nitrogen are generally preferred. Compounds of the formula (I) wherein $Z_2$ is $NH_2$ and $Z_1$ is hydrogen are generally preferred.

The following specific compounds of formula (I) are especially preferred:

1) (±)-exo-2-adenyl-endo-6-hydroxybicyclo[3,3,0]octane dihydrochloride,
2) (±)-exo-2-adenyl-endo-6-hydroxybicyclo[3,3,0]octane,
3) (±)-exo-5-(6-amino-purin-9-yl)-octahydropentalenediendo-1,6-diol,
4) (±)-exo-5-(6-amino-purin-9-yl)-octahydropentalenediendo-1,6-diol dihydrochloride,
5) (±)-exo-3-(6-amino-purin-9-yl)-octahydropentalenediendo-2,4-diol,
6) (±)-exo-3-(6-amino-purin-9-yl)-octahydropentalenediendo-2,4-diol dihyrochloride.

Certain groups and configurations are also preferred for compounds of formula (II) in their end-use application.

Compounds of the formula (II) wherein Y is nitrogen are generally preferred. Compounds of the formula (II) wherein $Z_2$ is $NH_2$ and $Z_1$ is hydrogen are generally preferred.

Certain groups and configurations are also preferred for compounds of formula (III) in their end-use application. Compounds of the formula (III) wherein Y is nitrogen are generally preferred. Compounds of the formula (III) wherein $Z_2$ is $NH_2$ and $Z_1$ is hydrogen are generally preferred.

The following specific compounds of formula (III) are especially preferred:

1) [3S, 6R]-6-(6-amino-purin-9-yl)-hexahydro-furo[3,2-b]furan-3-ol;
2) [3S, 6R]-6-(6-amino-purin-9-yl)-hexahydro-furo[3,2-b]furan-3-ol dihydrochloride;
3) [3R, 6R]-6-(6-amino-purin-9-yl)-hexahydro-furo[3,2-b]furan-3-ol;
4) [3R, 6R]-6-(6-amino-purin-9-yl)-hexahydro-furo[3,2-b]furan-3-ol dihydrochloride.

The following studies illustrate the utility of the compounds of formulas (I), (II) or (III). These studies are understood to be illustrative only and are not intended to limit the scope of the invention in any way. As used herein the following terms have the indicated meanings: "μM" refers to micromolar concentration; "Units" refers to the internationally accepted measurement of protein; "S.D." refers to standard deviation; "ηmol" refers to nanomoles; "ηg" refers to nanograms.

In Vitro Activity

Utilizing an in vitro cellular immunology-based assay which uses human peripheral blood and subsequent purification of monocyte-derived macrophages (according to the method of Edwards et al. *J. Cellular Biochemistry* 1993, 19E: 35), (±)-exo-2-adenyl-endo-6-hydroxybicyclo[3,3,0] octane dihydrochloride showed activity in proinflammatory cytokine inhibition. Monocyte-derived macrophages stimulated with bacterial lipopolysaccharide (LPS) produce high levels of TNF-α (25.8+4.2 ηg/mL) during 18 hours of culture. (±)-Exo-2-adenyl-endo-6-hydroxybicyclo[3,3,0] octane dihydrochloride was effective at inhibiting TNF-α levels in a dose response fashion (100 μM–0.1 μM) with an $IC_{50}$ value of 0.143+0.091 μM in comparison to the positive control compound used in this assay (Pentoxifylline [PTX]; inhibition at 50 μM=73.5%).

In Vivo Activity

Utilizing an in vivo immunology-based assay which uses a D-galactosamine animal model of septic shock (according to the method of Parmely et al. *European Cytokine Network*, vol.3, No.2, page 249, (±)-exo-2-adenyl-endo-6-hydroxybicyclo[3,3,0]octane dihydrochloride showed elevated activity in protecting mice against the lethal effects of LPS. Mice treated with the vehicle Hanks Balanced Salt Solution (HBSS) approximately 1 hour before intraperitoneal (i.p.) challenge of D-galactosamine and LPS, succumbed to disease by 18 hours after challenge (e.g. 6 out of 8 mice killed; 25% protection). However, mice treated with (±)-exo-2-adenyl-endo-6-hydroxybicyclo[3,3,0]octane dihydrochloride (100 mg/kg i.p., time=−1 hour) were afforded significantly ($p<0.05$ by $x^2$ analysis) enhanced protection (0 out of 8 mice killed; 100% protection). Positive-control PTX afforded decreased protection in this model (7 out of 8 mice killed; 12.5% protection).

What is claimed is:

1. A compound of the formula

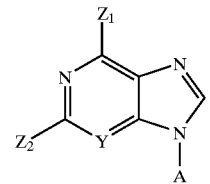

wherein

Y is nitrogen;

$Z_1$ and $Z_2$ are each independently hydrogen, halogen or $NH_2$; and

A is selected from the group consisting of:

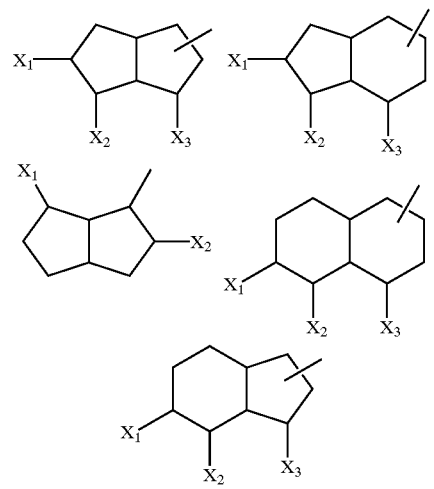

wherein $X_1$, $X_2$ and $X_3$ are each independently hydrogen, OH, $N_3$, $NH_2$, $N(R)_2$, NHR, CN, $CH_2NH_2$, $CONH_2$, $CO_2H$, $CH_2OH$, SH or SR;

wherein R is $C_1$–$C_4$ alkyl; and the pharmaceutically acceptable salts thereof;

with the proviso that at least one of $X_1$, $X_2$ or $X_3$ is other than hydrogen, and with the further proviso that when $Z_1$ is NH3; $Z_2$ is H or $NH_2$; A is

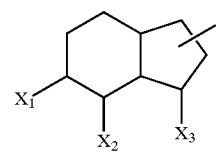

$X_3$ is H or OH; $X_2$ is H; then $X_1$ is not $CO_2H$.

2. A compound of the formula

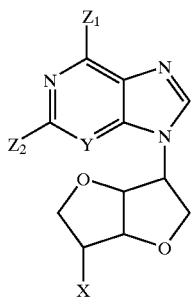

wherein

Y is nitrogen;

$Z_1$ and $Z_2$ are each independently hydrogen, halogen or $NH_2$; and

X is $N_3$, $NH_2$, $N(R)_2$, NHR, CN, $CH_2NH_2$, $CONH_2$, $CO_2H$, $CH_2OH$, SH or SR;
 wherein R is $C_1$–$C_4$ alkyl; and the pharmaceutically acceptable salts thereof.

3. A method of inhibiting the TNF-α activity in a patient in need thereof comprising administering to said patient an effective antiinflammatory amount of a compound of claims 1 or 2.

4. A compound according to claim 2 wherein $Z_2$ is hydrogen.

5. A compound according to claim 4 wherein $Z_1$ is $NH_2$.

6. A compound according to claim 1 wherein A is an octahydropentalene.

7. A compound according to claim 6 wherein $X_2$ is $N_3$.

8. A method according to claim 3 wherein the patient is suffering from AIDS.

9. A compound according to claim 2 wherein $Z_2$ is hydrogen.

10. A compound according to claim 9 wherein $Z_1$ is $NH_2$.

11. A compound according to claim 2 wherein X is $N_3$.

12. A method according to claim 3 wherein the patient is suffering from rheumatoid arthritis.

13. A compound according to claim 11 wherein $Z_2$ is hydrogen.

14. A compound of claim 1 wherein the compound is (±)-exo-2-adenyl-endo-6-hydroxybicyclo[3,3,0]octane dihydrochloride.

15. A compound of claim 1 wherein the compound is (±)-exo-5-(6-amino-purin-9-yl)-octahydropentalene-diendo-1,6-diol.

16. A compound of claim 1 wherein the compound is (±)-exo-3-(6-amino-purin-9-yl)-octahydropentalene-diendo-2,4-diol.

17. A method of inhibiting the TNF-α activity in a patient in need thereof comprising administering to said patient an effective antiinflammatory amount of a compound of the formula

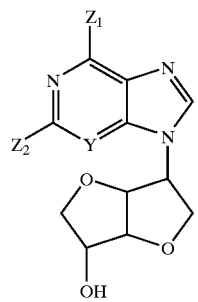

wherein

Y is nitrogen;

$Z_1$ and $Z_2$ are each independently hydrogen, halogen or $NH_2$; and the pharmaceutically acceptable salts thereof.

18. A method according to claim 3 wherein the patient is suffering from bacterial meningitis.

19. A method of claim 3 wherein the compound is (±)-exo-2-adenyl-endo-6-hydroxybicyclo[3,3,0]octane dihydrochloride.

20. A method of claim 3 wherein the compound is (±)-exo-5-(6-amino-purin-9-yl)-octahydropentalene-diendo-1,6-diol.

21. A method of claim 3 wherein the compound is (±)-exo-3-(6-amino-purin-9-yl)-octahydropentalene-diendo-2,4-diol.

22. A method of lowering tumor Necrosis Factor-α in a patient suffering from septic shock comprising administering to said patient an effective immunosuppressant amount of a compound of the formula

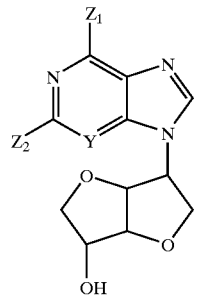

wherein

Y is nitrogen;

$Z_1$ and $Z_2$ are each independently hydrogen, halogen or $NH_2$; and the pharmaceutically acceptable salts thereof.

23. A method of lowering tumor Necrosis Factor-α in a patient suffering from septic shock comprising administering to said patient an effective immunosuppressant amount of a compound of claims 1 or 2.

24. A method of claim 23 wherein the compound is (±)-exo-2-adenyl-endo-6-hydroxybicyclo[3,3,0]octane dihydrochloride.

25. A method of claim 23 wherein the compound is (±)-exo-5-(6-amino-purin-9-yl)-octahydropentalene-diendo-1,6-diol.

26. A method of claim 23 wherein the compound is (±)-exo-3-(6-amino-purin-9-yl)-octahydropentalene-diendo-2,4-diol.

27. A method according to claim 17 wherein the patient is suffering from adult respiratory distress syndrome.

28. A method according to claim 3 wherein the patient is suffering from adult respiratory distress syndrome.

29. A method according to claim 17 wherein the patient is suffering from inflammatory bowel disease.

30. A method according to claim 3 wherein the patient is suffering from inflammatory bowel disease.

31. A method according to claim 17 wherein the patient is suffering from bacterial meningitis.

32. A method according to claim 17 wherein the patient is suffering from AIDS.

33. A method according to claim 17 wherein the patient is suffering from rheumatoid arthritis.

* * * * *